(12) United States Patent
Evans

(10) Patent No.: US 7,427,296 B2
(45) Date of Patent: Sep. 23, 2008

(54) TOTAL KNEE JOINT MOLD AND METHODS

(76) Inventor: Richard Parker Evans, 1356 Preserve Cir., Golden, CO (US) 80401

( * ) Notice: Subject to any disclaimer, the term of this patent is extended or adjusted under 35 U.S.C. 154(b) by 301 days.

(21) Appl. No.: 10/714,050

(22) Filed: Nov. 14, 2003

(65) Prior Publication Data

US 2005/0107885 A1 May 19, 2005

(51) Int. Cl.
*A61F 2/38* (2006.01)
(52) U.S. Cl. .................. 623/20.14; 623/20.15
(58) Field of Classification Search .... 623/20.14–20.15
See application file for complete search history.

(56) References Cited

U.S. PATENT DOCUMENTS

| | | | | |
|---|---|---|---|---|
| 4,209,861 A | * | 7/1980 | Walker et al. | 623/20.27 |
| 5,123,927 A | * | 6/1992 | Duncan et al. | 623/20.21 |
| 5,226,915 A | | 7/1993 | Bertin | |
| 5,480,444 A | | 1/1996 | Incavo et al. | |
| 5,639,279 A | * | 6/1997 | Burkinshaw et al. | 623/20.31 |
| 5,980,573 A | * | 11/1999 | Shaffner | 128/898 |
| 6,013,103 A | * | 1/2000 | Kaufman et al. | 623/20.15 |
| 6,342,075 B1 | | 1/2002 | MacArthur | |
| 6,355,705 B1 | | 3/2002 | Bond et al. | |
| 6,506,215 B1 | * | 1/2003 | Letot et al. | 623/20.29 |

* cited by examiner

*Primary Examiner*—Corrine McDermott
*Assistant Examiner*—Christopher D Prone
(74) *Attorney, Agent, or Firm*—Townsend and Townsend and Crew LLP

(57) ABSTRACT

In one embodiment, a method for treating an infected implant area of a knee joint comprises surgically accessing the implant area, and inserting a tibial component into the tibia using an antibiotic-impregnated material. A femoral component is formed that is configured to interact with the tibial component by stable knee joint articulation and motion. The femoral component is formed of an antibiotic-impregnated material using a mold. The femoral component is attached to the femur using an antibiotic-impregnated material, and the tibial component is interfaced with the femoral component to form a stable temporary knee joint capable of reducing the spread of infection while permitting movement of the knee joint.

16 Claims, 7 Drawing Sheets

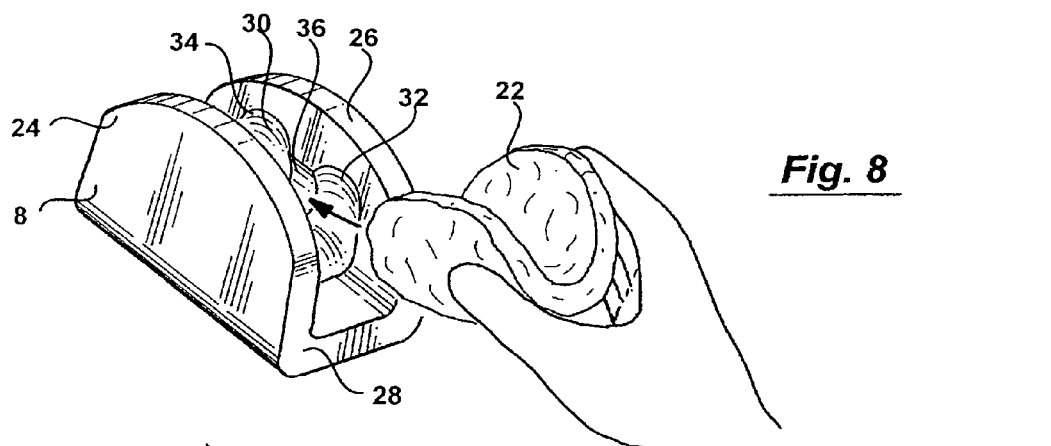
*Fig. 8*
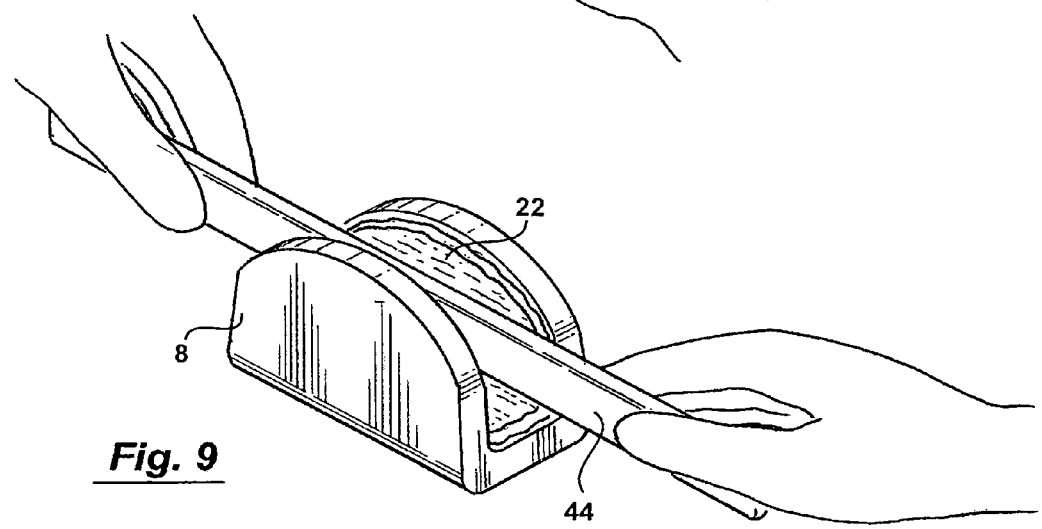
*Fig. 9*
*Fig. 10*
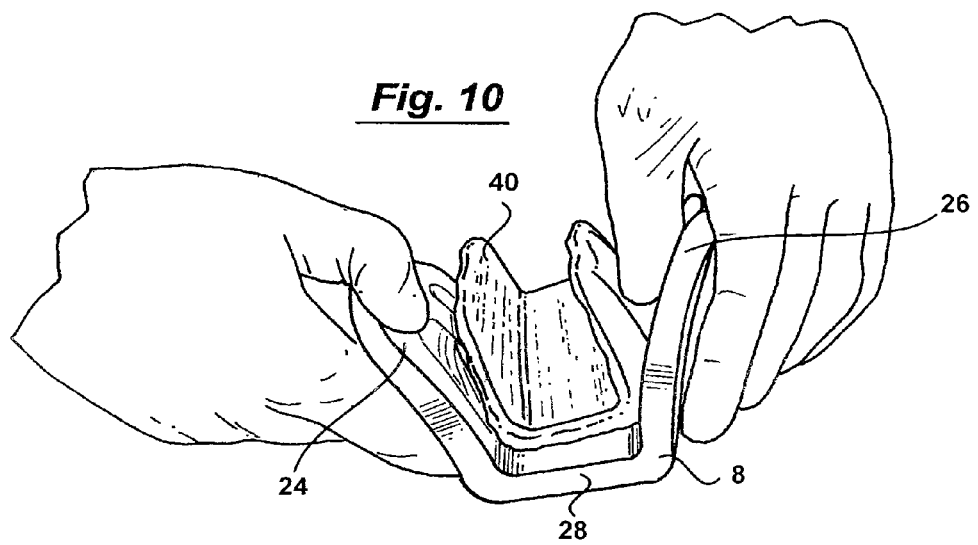

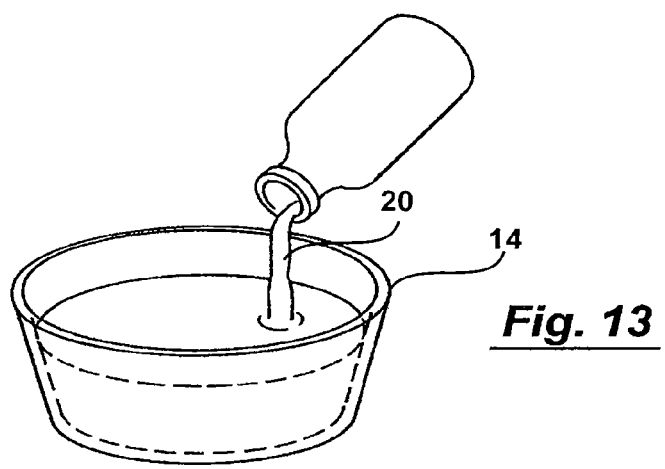
*Fig. 13*
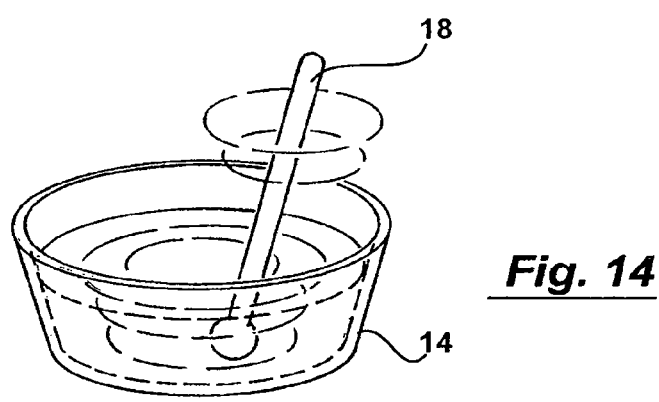
*Fig. 14*
*Fig. 15*
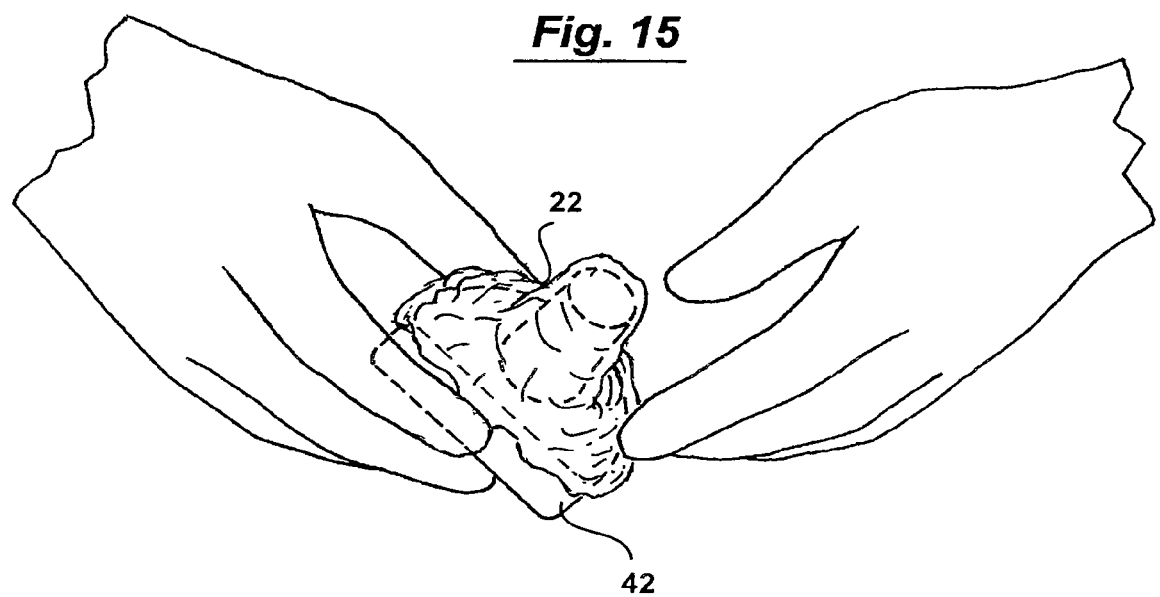

TOTAL KNEE JOINT MOLD AND METHODS

BACKGROUND OF THE INVENTION

This invention relates generally to the field of orthopedic surgery, and in particular to total knee replacements. More specifically, the invention relates to the treatment of an infected total knee replacement.

In the United States, about 600,000 total knee arthroplasty procedures (also known as total knee replacements) are performed each year. A typical total knee replacement procedure involves resurfacing of the tibial plateaus and the femoral condoyle. Holes are then drilled into the femur and the tibia. A metallic femoral component is then inserted into the femur and a metallic tibial component is inserted into the tibia. Bone cement usually holds the two components into place. These two components work together to replace the diseased knee joint and to simulate the function of a normal knee joint. One example of a total knee replacement surgery is described in U.S. Pat. No. 6,342,075, the complete disclosure of which is herein incorporated by reference.

About two to three percent of total knee replacements become deeply infected. When these components are simply replaced by new components, the rate of cure of the infection is low compared to a two-stage surgical treatment where the components are removed and the infection treated before new components are reimplanted. In such cases, some have proposed removing the femoral and tibial components and replacing them with a puck-shaped spacer or void shaped spacer made of bone cement that is impregnated with an antibiotic or a fixed mass of antibiotic impregnated cement that fills the dead space left by the removal of the infected prosthetic components. This is placed between the femur and the tibia for six to twelve weeks. The antibiotic in the puck or cement mass leaches out over time to treat the infection. When the infection is contained, the puck is removed and the femoral and tibial components are once again inserted. Such a process is described in U.S. Pat. No. 5,980,573, the complete disclosure of which is herein incorporated by reference.

One problem with the use of such a spacer is that there is no knee joint while the infection is being treated. As such, the leg cannot move or bend. Often the spacer is loose and painful and the knee will scar down and will stiffen up, resulting in painful rehabilitation, loss of final normal range of motion and function, among other ailments. This also makes the final replacement surgery itself technically more difficult because of the scarring and loss of motion and knee joint space at the time of reimplantation of new permanent components.

SUMMARY OF THE INVENTION

In one embodiment, the invention provides a method for treating an infected implant area of a knee joint. According to the method, the implant area is surgically accessed and any infected total knee replacement implants are removed from the implant area. This is completed with an aggressive surgical debridement of all infected tissue. A tibial component is inserted temporarily into the tibia and is secured using antibiotic-impregnated bone cement. The tibial component may comprise a posterior stabilized all polyethylene tibial component. A femoral component is sized and then formed, preferably during the surgery, of antibiotic-impregnated bone cement. This can be done by sculpting the femoral component by hand but a more uniform implant with a smoother articulating surface is obtained if the implant is formed using a mold device. To do so, a mold may be used to form the femoral component into the appropriate shape. The femoral component is temporarily attached to the femur using antibiotic-impregnated bone cement. The tibial component is interfaced with the femoral component to form a temporary knee joint capable of eluting high levels of antibiotics thus treating and reducing the spread of infection while permitting movement of the knee joint. In this way, the infection may be treated by local antibiotic elution as well as intravenous antibiotic elution while also providing movement of the leg at the knee joint. In this way, stiffening of the leg is generally prevented and knee joint range of motion is preserved thereby reducing pain during treatment and allowing more functional activity of daily living during the recovery time. This also improves the technical ease and success of the final operation of revision knee component implantation and the ultimate outcome of improved knee joint range of motion and overall function of the final knee replacement.

In one aspect, the tibial component may comprise a generally smooth articulating element that interfaces with the femoral component to minimize wear debris from the femoral component. For example, the tibial component may be constructed of polyethylene. In this way, the amount of wear experienced by the femoral component may be reduced as it interacts with the tibial component. Also, the femoral component is constructed so that it interfaces with the tibial component to stabilize the knee joint, thereby facilitating movement while the infection is being treated.

To form the femoral component, one or more powdered antibiotics may be combined with a polymer in powder form. A liquid activating agent is added to the mixture to form the antibiotic-impregnated material. The resulting antibiotic-impregnated material is like dough, and is placed into the mold where it is formed into the shape of the femoral component. The size of the component required is preferably determined at surgery. Once shaped, the mold is removed and the femoral component is permitted to harden. If needed, edges of the femoral component may be trimmed. Preferably, the femoral component is formed into the shape of an articulating femoral prosthesis. The femoral and tibia components are temporarily secured to the bone using antibiotic-impregnated bone cement. In this way, the antibiotic leaches out to treat the infection. Before the components are attached to the bone, however, the bone cement is allowed to partially cure so that bone cement does not significantly interdigitate with the bone and so the components may be removed without damaging the bone. In some cases, the femoral component may be hand made without a mold. In such cases, the cement is rolled flat, trimmed into the same shape that the removed femoral component would assume if rolled flat, and then wrapped into the widely exposed distal femur after partial curing. The cement is rolled into a thickness that will accommodate the femoral bone defect resulting from debridement of the component. The cement is pressed into place, trimmed and the articulating surface of the cement implant is hand molded to the same shape as the removed infected prosthesis. After the cement femoral component cures, the non-articulating surface of a posterior stabilized prosthesis may be wrapped in cement and implanted as described herein.

After the infection has subsided and determined to be infection free, the implant area may be re-accessed, and the femoral and tibial components may be removed and replaced with a permanent femoral prosthesis and a tibial prosthesis. Because the bone cement was allowed to partially cure, the components may easily be removed.

In another embodiment, the invention provides a temporary knee prosthesis that comprises a femoral component comprising an antibiotic impregnated bone cement that is formed in the shape of a femoral knee joint using a mold. The bone cement is placed into the mold, permitted to harden and then removed from the mold. In one aspect, the bone cement may comprise a polymethylmethacrylate material combined with an antibiotic. This bone cement allows the antibiotic to elute from the bone cement at higher levels than can be obtained from the standard and simultaneous intravenous antibiotic administration that is administered routinely for four to six weeks. The antibiotics eluted also penetrate and treat avascular tissue that intravenous antibiotics cannot reach, thus increasing the overall success rate of the two stage treatment over a simple one stage exchange of components. Such a mold provides the appropriate geometrical shape of the femoral component that allows articulation and movement of the knee joint during the treatment period. Additionally, the femoral component made from such a mold provides a smooth surface on the femoral component which decreases friction of the femoral component and tibial component articulation or movement during the treatment period. This smooth geometric shape formed by the mold allows a greater range of motion of the knee to be maintained during treatment and decreases friction of the components and therefore the wear debris of the femoral and tibial articulation during movement in the treatment period. This is desirable because the wear debris cannot often be entirely removed at the final stage of surgery and becomes a residual foreign body that may aggravate treatment of the infection or even become a focus of a new infection after the antibiotics have eluted from the cement debris.

The femoral component may be part of a kit that also includes a tibial component that is made of a smooth material, such as a polyethylene, to prevent wear of the femoral component. A posterior stabilized tibial component configuration adds knee joint stability to the knee motion during treatment.

BRIEF DESCRIPTION OF THE DRAWINGS

FIG. 8 illustrates the placement of the bone cement into a mold.

FIG. 9 illustrates how the bone cement is formed in the mold.

FIG. 10 illustrates the removal of the resulting femoral component from the mold.

FIGS. 13 and 14 illustrate a method for making more antibiotic impregnated bone cement.

FIG. 15 illustrates a method for placing the bone cement onto the tibial component.

DESCRIPTION OF THE SPECIFIC EMBODIMENTS

The invention provides exemplary techniques and kits that may be used to treat an infected implant area resulting from a total knee replacement procedure. Following diagnosis of the infection, the implant area needs to be surgically accessed. This may be accomplished by forming a long incision on the front of the knee to expose the previously inserted femoral and tibia prostheses that form the knee replacement. This incision is typically through the scar of the original component implantation procedure. All infected total knee replacement implants are removed and a radical soft and hard tissue debridement is performed.

The implants are replaced with temporary implants that are used to fight the infection. One of the implants may be constructed of bone cement impregnated with an antibiotic while the other is made of a material that interfaces with the bone cement implant without causing excessive wear of the bone cement implant. This may be done during the surgical procedure to permit the surgeon to determine the proper size of the implant while the femur and the tibia are exposed. Both implants may be temporarily attached to the femur and the tibia using the antibiotic impregnated bone cement to help fight the infection. In so doing, the bone cement is allowed to sufficiently cure or harden so that the cement does not excessively interdigitate with the bone when the temporary components are inserted. Thus when the implants are subsequently removed, the bone cement will not tear away excessive bone and other tissue. Also, the implants are configured in a shape that permits movement of the leg at the knee joint while also providing stability, posterior as well as medial and lateral. This permits stable movement in the leg to help prevent the leg from stiffening up while the temporary implants are in place. Once the infection has been treated, the knee is again opened, the temporary implants are removed and permanent knee replacement implants are put back in. As just described, by allowing the bone cement to somewhat harden before attaching the implants to the femur and the tibia, the implants may easily be removed without damaging the tissue and preserving the bone stock needed to perform adequate revision implantation of permanent components. In this way, the new revision knee replacement prosthetics may more easily be attached and implanted, thereby reducing surgery time and improving the final outcome per standard total joint replacement analysis.

Figure 1:
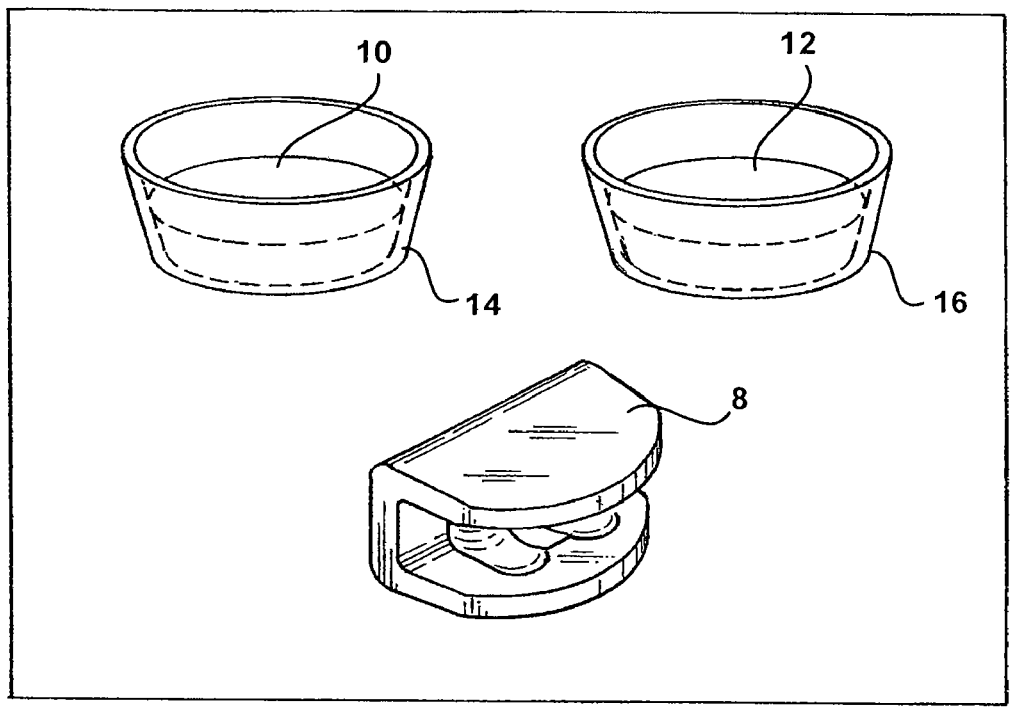
FIG. 1 illustrates a kit that may be used to make a femoral component when treating an infected area associated with a total knee replacement according to the invention.

Referring now to the figures, one exemplary method for performing such a procedure will be described. In FIG. 1, an incision has already been made in the patient's knee and the knee joint implants have been removed. The temporary femoral component is ready to be produced using a mold 8. This process utilizes an antibiotic impregnated material. This is made from two anesthetic agents 10 and 12 that are stored within containers 14 and 16. For example, agent 10 may comprise one kind of antibiotic while component 12 may comprise another kind of antibiotic. Conveniently, agent 10 may comprise powdered tobramycin, and agent 12 may comprise powdered vancomycin, commercially available from a variety of pharmaceutical companies. However it will be appreciated that other types of antibiotics may be used as well if they are heat stable, elute from the bone cement and are desired to more specifically treat a given infectious organism that has been identified.

Figure 2:
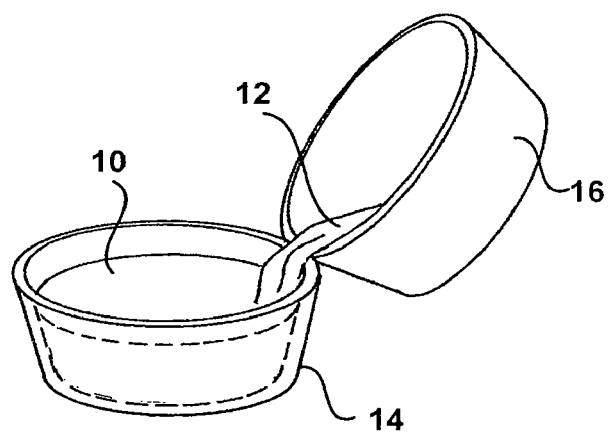
FIG. 2 illustrates a method for dividing an antibiotic/bone cement powder according to the invention.
Figure 3:
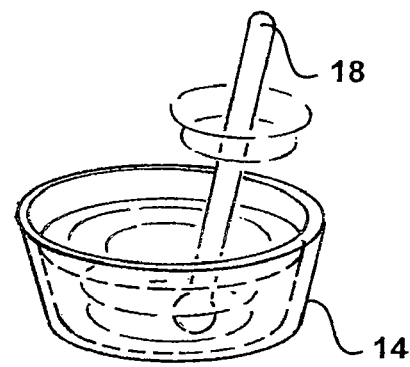
FIG. 3 illustrates a method for mixing the antibiotic with the bone cement.

As shown in FIG. 2, agents 10 and 12 are combined and powdered bone cement is also added. Often the antibiotics obtained are granular and can be made into a finer powder once again by pushing the powder through a standard commercially available cement screen. These are mixed with the bone cement which is also in powder form, and is preferably a methylmethacrylate polymer, commercially available from a number of companies. One preferred type of bone cement is Palacos bone cement, commercially available from _____. This bone cement has been shown to have exemplary antibiotic elution characteristics by a number of studies. The ingredients are mixed together using a stirrer 18 as shown in FIG. 3. The mixture may then be divided by pouring halfback into container 14 for later use as described hereinafter.

Figure 4:
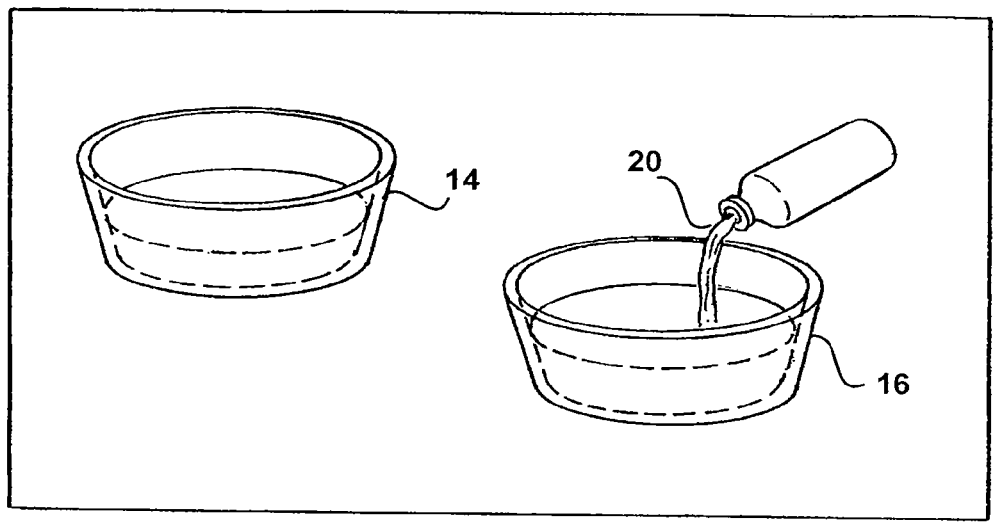
FIG. 4 illustrates a method for adding an activating agent to the antibiotic/bone cement mixture.
Figure 5:
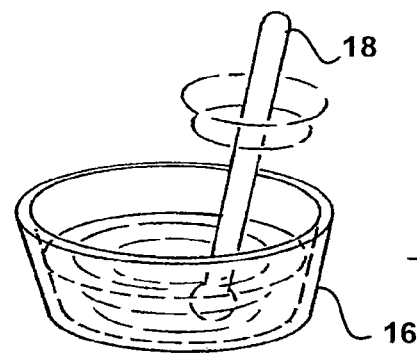
FIG. 5 illustrates a method for mixing the activating agent with the bone cement mixture.

In FIG. 4, an activating agent 20 (the monomer universally provided with each bone cement kit) is added to the mixture and reacts with the bone cement to form polymethylmethacrylate 22 (also referred to as PMMA). The mixture is stirred with stirrer 18 until the PMMA 22 has a doughy consistency as shown in FIG. 5. Although described using one type of bone cement with specific types of antibiotics, it will be appreciated that other bone cements and antibiotic agents may be used, including those described in U.S. Pat. No. 6,355,705, the complete disclosure of which is herein incorporated by reference.

Figure 6:
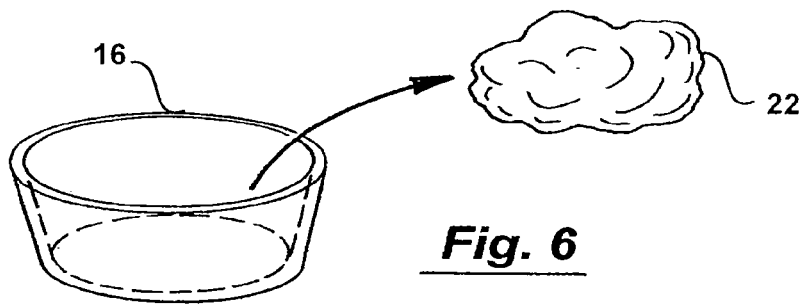
FIGS. 6 and 7 illustrates a method for shaping the resulting bone cement.
Figure 7:
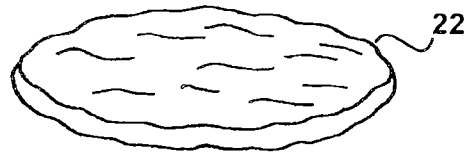

In FIG. 6, the PMMA 22 is removed from container 16 and formed into a pancake shape as shown in FIG. 7. The PMMA 22 is then placed into mold 8 as shown in FIG. 8. Mold 8 has a pair of sides 24 and 26 and a bottom 28, and is constructed of a flexible material, such as a medical grade plastic to permit sides 24 and 26 to be flexed away from each other. Formed in mold 8 is a cavity 30 that is in the shape of the exterior of a traditional femoral prosthesis that has been modified (thickened throughout) to provide greater strength to the cement femoral component. As shown, cavity 30 includes two outer arched sections 32 and 34 and an inner section 36. This configuration is used to produce a femoral component 40 that interfaces with a tibial component 42 as described hereinafter (see FIG. 12). However, it will be appreciated that other shapes of femoral components may be produced as well, including those known in the art and those described in U.S. Pat. Nos. 5,226,915 and 6,506,215, the complete disclosures of which are herein incorporated by reference.

Figure 11:
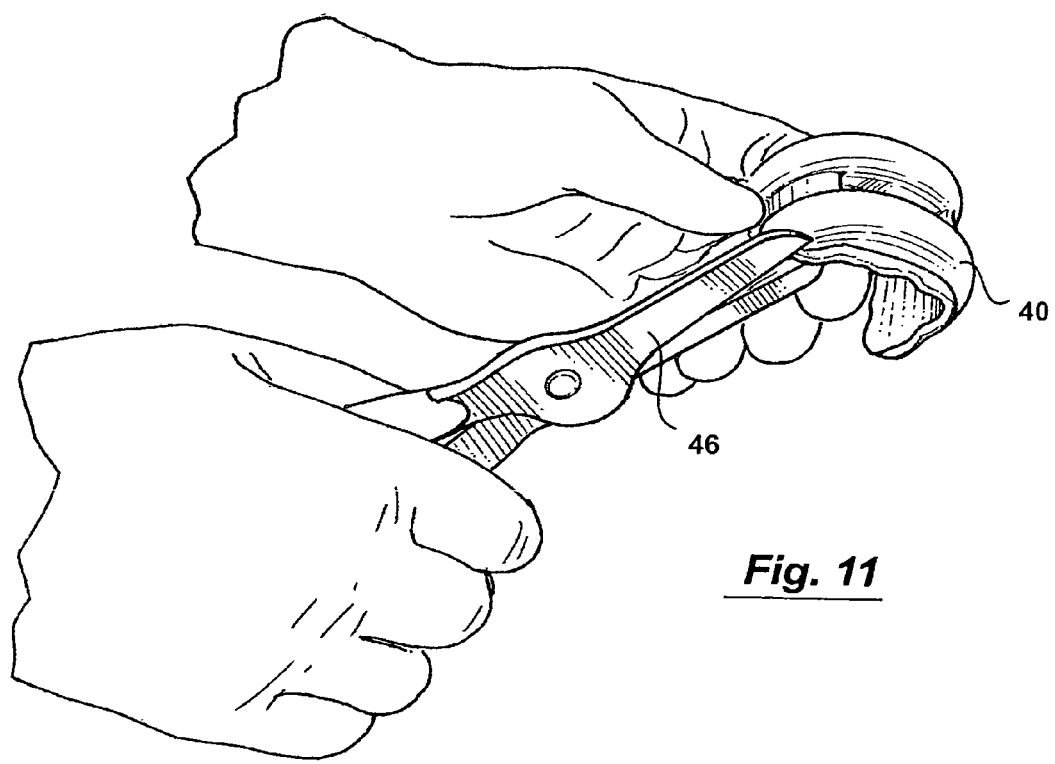
FIG. 11 illustrates the removal of excess material from the femoral component.

As shown in FIG. 9, the PMMA 22 is pressed into cavity 30 and a straight edge 44 is used to smooth the back side of the PMMA 22. Once formed in the desired shape, sides 24 and 26 are pulled away from each other as shown in FIG. 10 to permit the femoral component 40 to be removed from mold 8. When removed from mold 8, femoral component 40 is still somewhat soft to permit any unwanted edges to be trimmed using scissors 46 as shown in FIG. 11. The approximate time from mixing to removal from the mold is about three minutes to about ten minutes depending on the cement used, the amount and type of antibiotics mixed into the cement and the room temperature. Femoral component 40 is typically hard enough to be attached to the femur after about five minutes to about fifteen minutes from the time of mixing.

Figure 12:
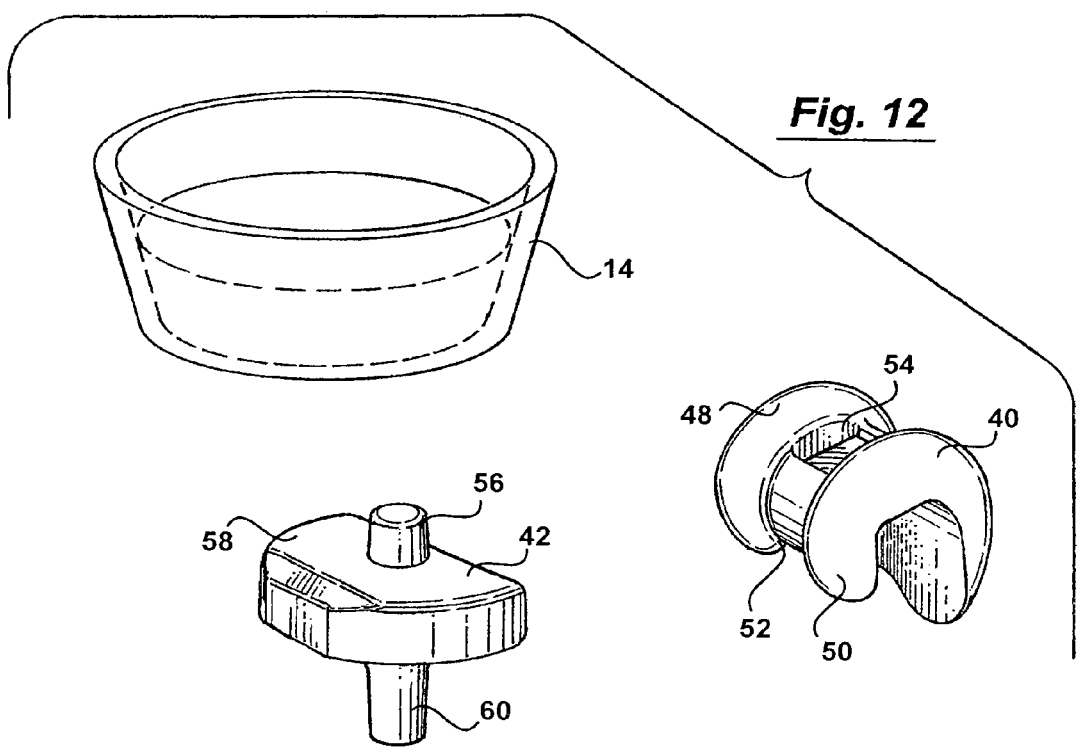
FIG. 12 illustrates the femoral component of FIG. 11 along with a tibial component.

As best shown in FIG. 12, femoral component has two outer rails 48 and 50 and a center section 52. Formed in center section 52 is a recess 54 for receiving the posterior stabilizing protrusion 56 on tibial component 42. Tibial component 42 also includes a tray 58 and a central stem 60 that fits within the tibia. In use, protrusion 56 fits within recess 54 and rails 48 and 50 sit on tray 58. In this way, femoral component 40 and tibial component 42 may articulate with respect to each other while providing posterior as well as lateral and medial stability to the knee joint. Tibial component 42 may also be constructed of a material that will not cause excessive wear on femoral component 40. One example of a material is polyethylene. Hence, when the two components are interfaced with each other, the knee joint may articulate without degrading or breaking the relatively fragile femoral component 40. This permits the patient to be able to articulate the leg while the infection is being treated.

With femoral component 40 sufficiently hardened, it is ready to be attached to the femur. To do so, container 14 which holds the reserved half of the antibiotic-laden bone cement is combined with activating agent 20 as shown in FIG. 13. This is then mixed with stirrer 18 (see FIG. 14) in essentially the same was as previously described to provide more PMMA. At this point, timing is critical. The PMMA will be used both to attach tibial component 42 to the tibia and femoral component 40 to the femur. However, since both of these components will be removed once the infection has been treated (in about 6 to 12 weeks); they need to be cemented in such a way that they can be removed without causing significant tissue damage. As such, the PMMA 22 is allowed to cure to the point where it still has adhesive qualities, but yet does not provide excessive bonding or bone recess interdigitation so that the two prostheses may easily be removed and replaced with their permanent counterparts. Typically, the PMMA 22 will be used within a window of about two minutes to about five minutes after mixing again depending on the cement type used, the amount and type of antibiotics mixed into the cement and the room temperature.

Figure 16:
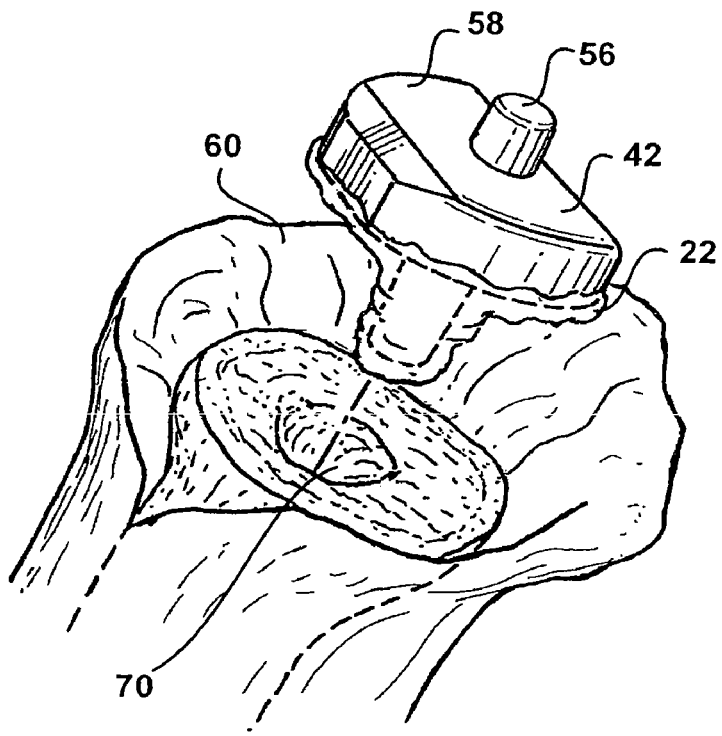
FIGS. 16 and 17 illustrate a method for inserting the tibial component into the tibia.
Figure 17:
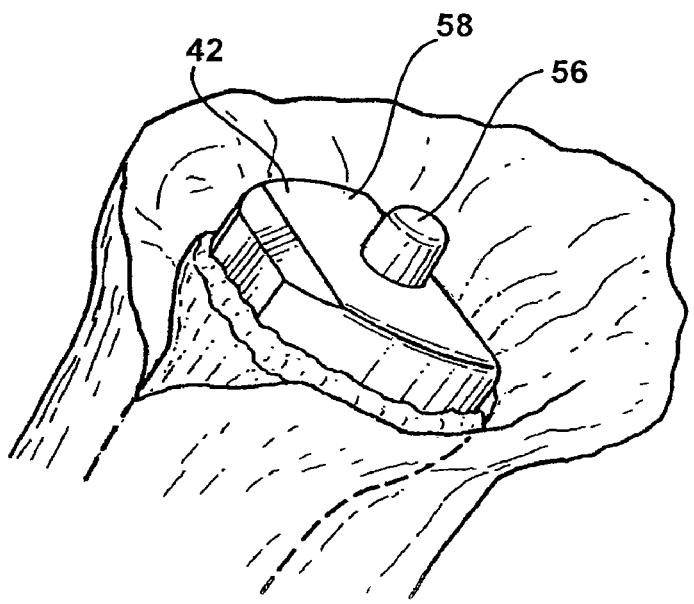

As shown in FIG. 15, the semi-cured PMMA 22 is formed around stem 60 and the bottom of tray 58 to a thickness of about one quarter inch to about one half inch. At this point, the PMMA 22 is quickly setting and the surgeon is just able to form it around stem 60. As shown in FIGS. 16 and 17, tibial component 42 and the applied antibiotic cement are pressed into the tibia, with stem 60 extending into the intramedullary canal 70. Excess cement extrude during the insertion process is removed.

Figure 18:
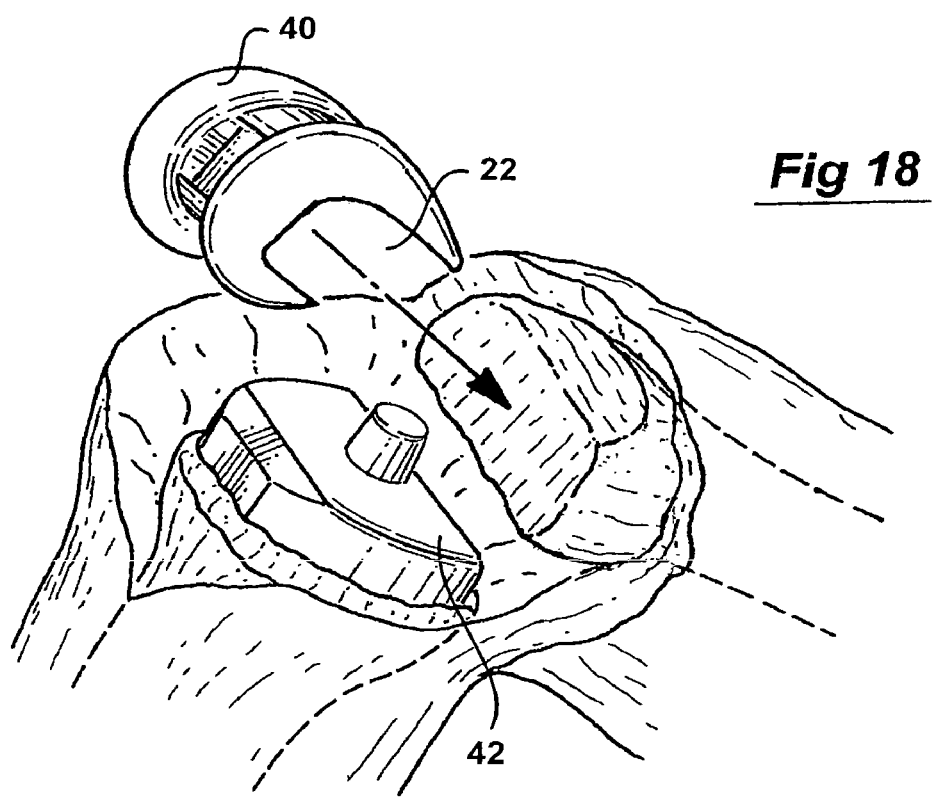
FIG. 18 illustrates a method for attaching the femoral component to the femur using bone cement.
Figure 19:
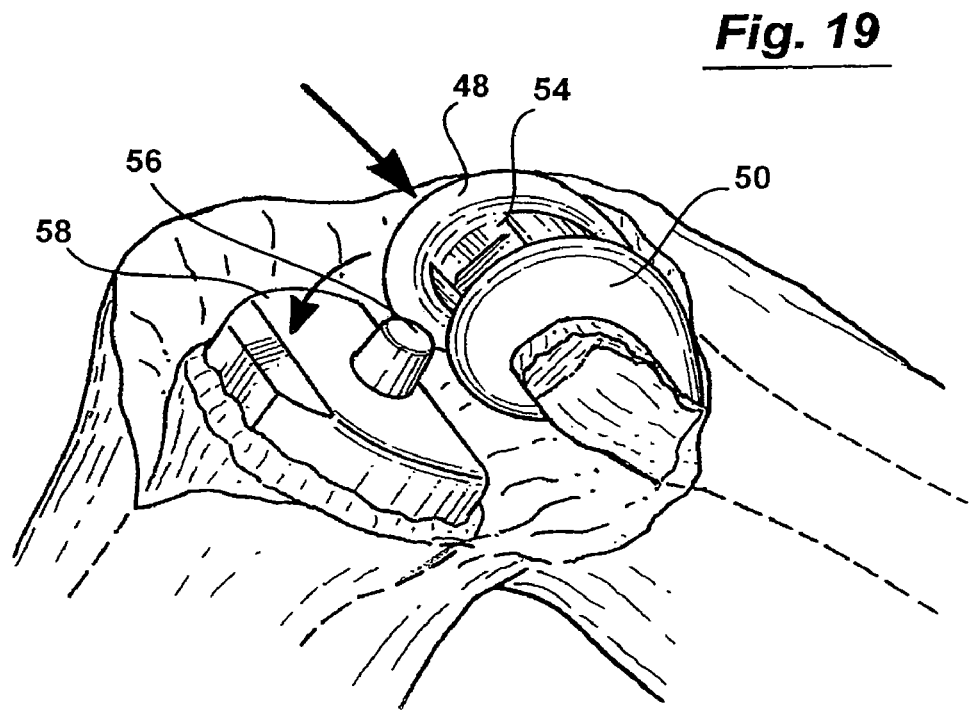
FIG. 19 illustrates the step of interfacing the tibial component with the femoral component.

More of the semi-cured PMMA 22 is also placed on the back side of femoral component 40 to a thickness of about one quarter inch to about one half inch as shown in FIG. 18. Femoral component 40 is then placed over the bottom of the femur as shown in FIG. 19. The protrusion 56 is then immediately placed into recess 54 and the leg is straightened so that rails 48 and 50 may roll over tray 58. Excess cement extrude during the insertion process is removed. The incision is then closed. The surgeon preferably moves the knee prior to and after wound closure to ensure adequate articulation occurs as planned.

The patient should be able to and is encouraged to bend the leg at the knee. This helps to prevent the build up of scar tissue and the leg from stiffening. As previously described, the two components provide stability to the knee joint to facilitate its articulation. The bone cement used to form the femoral component 40 as well as the bone cement used to attach the two components to the tibia and the femur leach out over time to fight the infection. Although the femoral component can withstand the weight of the patient's leg and forces concomitant to normal activities of daily living the cement femoral component may not be strong enough to withstand full weight bearing and the patient is discouraged to do so. Rather the patient uses ambulatory aides such as crutches or a walker until the second surgery when permanent components are implanted.

Once the infection has been treated, the knee may again be opened and the femoral component 40 and the tibial component 42 removed. As previously mentioned, the bone cement used to attach the two components to the bone was semi-cured, permitting the two components to easily be pulled from the bone without causing significant damage. The previously removed knee joint prosthesis may then be replaced with revision total knee components as is known in the art. Because little or no damage was caused by the temporary prostheses and because joint space and range of motion was maintained this process is relatively easy and comparable to a noninfected one stage revision knee replacement typically performed for component loosening or mechanical failure.

The invention has now been described in detail for purposes of clarity and understanding. However, it will be appreciated that certain changes and modifications may be practiced within the scope of the appended claims.

What is claimed is:

1. A method for treating an infected implant area of a knee joint, the method comprising:

surgically accessing the implant area;

inserting a tibial component into the tibia using an antibiotic-impregnated material, wherein the tibial component comprises a tray, a central stem that is inserted into a opening in the tibia and a posterior stabilizing protrusion, and wherein the antibiotic-impregnated material is placed onto the central stem so as to be within the opening in the tibia, wherein placement of the central stem into the opening in the tibia provides stability to the tibial component while attached to the tibia;

while the implant area is surgically accessible, forming a femoral component that is configured to interact with the tibial component, wherein the femoral component is formed of an antibiotic-impregnated material using a mold having a smooth U-shaped back surface with a recess for receiving the antibiotic-impregnated material, and wherein the femoral component comprises a single integral piece that is constructed of two outer surfaces that are spaced apart from each other by a center section having a recess to form a one-piece structure that resurfaces the entire distal femur, wherein the femoral component has a front surface that interfaces with the tibial component and a back surface that interfaces with the femur, wherein the back surface is generally smooth and does not include protrusions such that all areas of the back surface which interface with the femur are without protrusions, and wherein the step of forming the femoral component further comprises pressing the antibiotic-impregnated material into the mold to form the antibiotic-impregnated material in the shape of the femoral component, removing excess antibiotic-impregnated material from the U-Shaped back surface and smoothing the entire back surface of the femoral component using a straight edge which provides the femoral component to be temporarily contacted with the femur, and then removing the mold and permitting the femoral component to harden;

attaching the femoral component to the femur using an antibiotic-impregnated material such that the femoral component does not project into the femur; and interfacing the tibial component with the femoral component by placing the posterior stabilizing protrusion of the tibial component into the recess of the femoral component, with the two outer surfaces of the femoral component resting on the tray to form a temporary knee joint capable of treating an infection and reducing the spread of infection while permitting movement of the knee joint, with the two outer surfaces, recess and protrusion providing anterior and posterior as well as lateral and medial stability to the knee joint and maintaining the knee joint space, thereby reducing scarring and thus facilitating final implantation.

2. A method as in claim 1, wherein the tibial component comprises a generally smooth articulating element that interfaces with the femoral component to minimize wear on the femoral component.

3. A method as in claim 2, wherein the tibial component is constructed of polyethylene.

4. A method as in claim 1, wherein the step of forming the femoral component further comprises mixing a bone cement in powder form with at least one powdered antibiotic and adding a liquid activating agent to form the antibiotic-impregnated material.

5. A method as in claim 1, wherein the femoral component is formed into the shape of an articulating femoral prosthesis.

6. A method as in claim 1, further comprising re-accessing the implant area after the infection has been treated, removing the femoral and tibial components and inserting a femoral prosthesis and a tibial prosthesis.

7. A method as in claim 1, further comprising removing any infected total knee replacement implants after accessing the implant area.

8. A method as in claim 1, further comprising trimming the femoral component after removing it from the mold.

9. A method for treating an infected implant area of a knee joint, the method comprising:

surgically accessing the implant area;

removing an infected total knee replacement implant;

inserting a tibial component into the tibia using an antibiotic-impregnated material, wherein the tibial component comprises a tray, a central stem that is inserted into a opening in the tibia and a posterior stabilizing protrusion, and wherein the antibiotic-impregnated material is placed onto the central stem so as to be within the opening in the tibia, wherein placement of the central stem into the opening in the tibia provides stability to the tibial component while attached to the tibia;

forming a one-piece femoral component that is configured to interact with the tibial component, wherein the femoral component is formed of an antibiotic-impregnated material using a mold while the implant area is accessible and wherein the femoral component comprises a single integral piece that is constructed of two outer surfaces that are spaced apart from each other and connected by a center section having a recess, wherein the femoral component has a front surface that interfaces with the tibial component and a back surface that interfaces with the femur, wherein the back surface is generally smooth and does not include protrusions such that all areas of the back surface which interface with the femur are without protrusions, and wherein the step of forming the femoral component further comprises pressing the antibiotic-impregnated material into the mold to form the antibiotic-impregnated material in the shape of the femoral component, removing excess antibiotic-impregnated material from a U-Shaped back surface of the mold and smoothing the entire back surface of the femoral component using a straight edge which provides the femoral component to be temporarily contacted with the femur, and then removing the mold and permitting the femoral component to harden;

attaching the femoral component to the femur using an antibiotic-impregnated material with the femoral component resurfacing the entire distal femur and such that the femoral component does not project into the femur; and interfacing the tibial component with the femoral component by placing the posterior stabilizing protrusion of the tibial component into the recess of the femoral component, with the two outer surfaces resting on the tray to form a temporary knee joint capable of reducing the spread of infection while permitting movement of the knee joint with the two outer surfaces, recess and protrusion providing anterior, posterior as well as lateral and medial stability to the knee joint.

10. A method as in claim 9, wherein the tibial component comprises a generally smooth articulating element that interfaces with the femoral component to minimize wear on the femoral component.

11. A method as in claim 10, wherein the tibial component is constructed of polyethylene.

12. A method as in claim 9, wherein the step of forming the femoral component further comprises mixing a bone cement in powder form with a powdered antibiotic and adding a liquid activating agent to form the antibiotic-impregnated material.

13. A method as in claim 12, wherein the step of forming the femoral component further comprises pressing the antibiotic-impregnated material into the mold to form the antibiotic-impregnated material in the shape of the femoral component and then removing the mold and permitting the femoral component to harden.

14. A method as in claim 9, wherein the femoral component is formed into the shape of an articulating femoral prosthesis.

15. A method as in claim 9, further comprising re-accessing the implant area after the infection has been treated, removing the femoral and tibial components and inserting a permanent revision femoral prosthesis and a tibial prosthesis.

16. A method as in claim 9, further comprising trimming the femoral component after removing it from the mold.

* * * * *